United States Patent [19]

Okada

[11] Patent Number: 4,798,591
[45] Date of Patent: Jan. 17, 1989

[54] CATHETER OBTURATOR

[75] Inventor: Yosuke Okada, Mori, Japan

[73] Assignee: Sherwood Medical Company, St. Louis, Mo.

[21] Appl. No.: 943,273

[22] Filed: Dec. 17, 1986

[30] Foreign Application Priority Data

Dec. 18, 1985 [JP] Japan ................................ 60-284729

[51] Int. Cl.⁴ .............................................. A61M 5/00
[52] U.S. Cl. ................................... 604/164; 604/165; 604/281
[58] Field of Search ................... 604/164–170, 604/256, 95, 280–282, 104, 105; 129/207.14, 207.15; 128/341, 343

[56] References Cited

U.S. PATENT DOCUMENTS

| 3,809,081 | 5/1974 | Loveless | 604/170 |
| 3,923,066 | 12/1975 | Francisoud | 604/170 |
| 3,970,090 | 7/1976 | Loiacond | 604/104 |
| 4,315,513 | 2/1982 | Nawash et al. | 604/256 |
| 4,572,186 | 2/1986 | Gould et al. | 128/341 |

FOREIGN PATENT DOCUMENTS

| 0592182 | 4/1925 | France | 128/341 |
| 0688450 | 3/1953 | United Kingdom | 604/256 |

Primary Examiner—Dalton L. Truluck
Assistant Examiner—Denise Whelton
Attorney, Agent, or Firm—Stanley N. Garber; Andrew J. Beck; Montgomery W. Smith

[57] ABSTRACT

The present invention a catheter obturator including a stopper having a bore formed therethrough, a tube of resilient material connected at one end with the stopper to communicate with the bore in the stopper, the opposite end of the tube being closed, and manipulating means including a rigid rod adapted to be inserted into the tube, whereby when the rigid rod is moved forwardly in the tube, the latter can be elongated to facilitate the insertion of the tube into a catheter while when the rigid rod is removed out of the tube, the latter tends to return to its original form to fully close the internal bore of the catheter.

5 Claims, 1 Drawing Sheet

CATHETER OBTURATOR

BACKGROUND OF THE INVENTION

1. Field of the Invention

The present invention relates to improvements of an obturator inserted into a self-retaining catheter in a living body such that the blood reversed into the self-retaining catheter will be prevented from coagulating in the catheter.

2. Description of the Prior Art

One of such obturators in the prior art is shown in FIG. 5 of the accompanying drawings. The obturator includes a solid rod-like member 1 of a plastic material. To fully close the internal bore of a catheter, the external diameter of the rodlike member 1 must be equal to or larger than the internal diameter of the catheter. However, this provides a great difficulty in inserting the rod-like member 1 into the catheter. Therefore, a rod-like member having its external diameter slightly smaller than the internal diameter of the catheter is actually used. As a result, blood moved and stayed between the inner wall of the catheter and the outer periphery of the rodlike member has coagulated frequently.

SUMMARY OF THE INVENTION

It is therefore an object of the present invention to an improved catheter obturator which can easily be inserted into a catheter and yet fully close the internal bore of the catheter.

To this end, the present invention provides a catheter obturator comprising a stopper having a bore formed therethrough, a tube of resilient material connected at one end with said stopper to communicate with said bore in said stopper, the opposite end of said tube being closed, and manipulating means including a rigid rod adapted to be inserted into said tube.

In such an arrangement, prior to the insertion of the obturator into a self-retaining catheter, the rigid rod is inserted into the resilient stopper through its bore. After the forward end of the rigid rod has engaged the forward and inner end of the tube, the rigid rod is further moved forwardly to elongate the resilient tube. As a result, the external diameter of the resilient tube will be smaller than the internal diameter of the catheter. When the elongated tube is easily inserted into the self-retaining catheter with the rigid rod held in the tube, the removal of the rigid rod out of the tube causes the tube to return to its original form under the action of its own resiliency. Thus, the outer wall of the tube will sealingly engage the inner wall of the catheter to fully close the bore thereof.

DETAILED DESCRIPTION OF PREFERRED EMBODIMENTS

Figure 1:
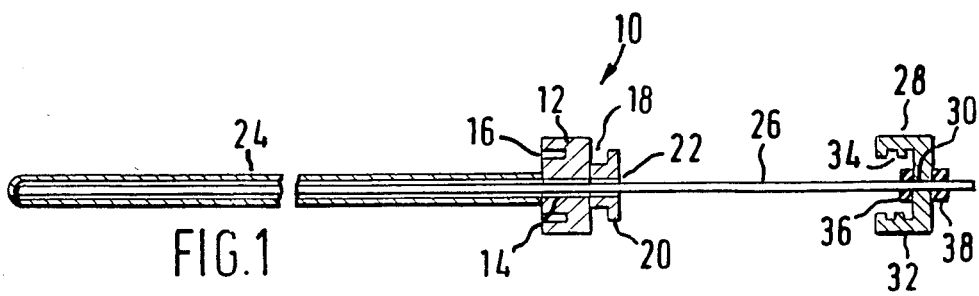
FIG. 1 is a longitudinal section of a catheter obturator constructed in accordance with the present invention.

Referring to FIG. 1, there is shown a catheter obturator 10 comprising a stopper 12 which is formed with a bore 14 extending therethrough in the axial direction. The forward face of the stopper 12 (shown leftwardly in FIG. 1) is provided with an annular groove 16 adapted to engage the outer end of a self-retaining catheter as in the prior art. The opposite or rearward face of the stopper 12 includes a boss 18 axially extending outwardly therefrom. The boss 18 has an annular flange 20 formed thereon at its outer end and having an outer threaded periphery. The boss 18 also includes a bore 22 formed axially therethrough, the bore 22 aligned with the bore 14 in the stopper 12.

The catheter obturator 10 also includes a tubular member 24 of a resilient material fixedly secured at one end to the forward face of the stopper 12. The opposite or forward end of the resilient tube 24 is closed.

The catheter obturator 10 further includes manipulating means 28 which includes a rigid rod 26 adapted to be inserted into the tube 24. The rigid rod 26 will be inserted into the tube 24 through the bores 14 and 22 in the stopper 12. The manipulating means 28 also includes a cap nut member 32 having an opening 30 formed therethrough, through which the rigid rod 26 also is passed. The cap nut member 32 has an internal threaded portion 34 which is adapted to threadingly engage the external threaded flange 20 of the boss 18 on the stopper 12. Resilient bushing elements 36 and 38 are respectively mounted on the opposite walls around the inner and outer ends of the bore 30 and serve as seals about the rigid rod 26 when it is passed through the bore 30.

Figure 2:
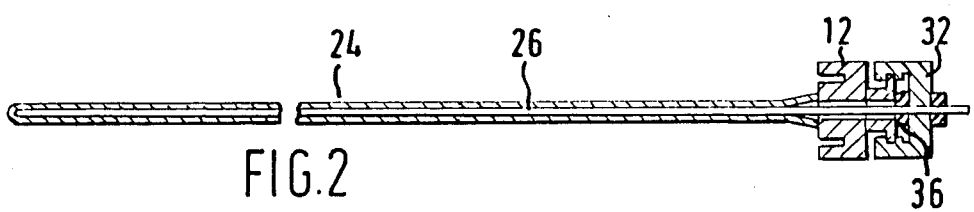
FIG. 2 is a view similar to FIG. 1, showing the obturator in its different position.

On operation, the rigid rod 26 is first passed through the bore 30 in the cap nut 32. The rigid rod 26 is then inserted into the tube 24 through the through-bores 14 and 22 in the stopper 12. When the rigid rod 26 is moved forwardly in the tube 24, the latter is elongated to reduce its external diameter as shown in FIG. 2. To maintain the rigid rod 26 at a position shown in FIG. 2, the cap nut 32 is threadingly engaged over the threaded flange 20 of the boss 18 on the stopper 12. Under such a state, the inner bushing element 36 is compressed into a deformed configuration to more rigidly engage the bushing element 36 around the outer periphery of the rigid rod 26.

Figure 3:
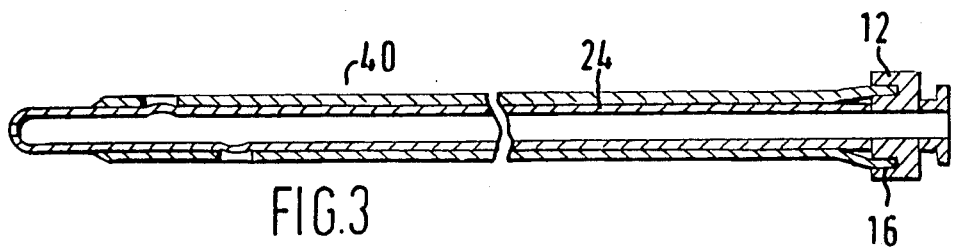
FIG. 3 is a longitudinal section of a self-retaining catheter into which the obturator shown in FIGS. 1 and 2 is inserted.

Thereafter, the obturator 10 is inserted into, for example, a self-retaining catheter 40 as shown in FIG. 3. When the rigid rod 26 is released under such a state, the tube 24 tends to return to its original form under its own resiliency. As a result, the external diameter of the tube 24 will be increased into engagement with the inner wall of the self-retaining catheter 40 to fully close the internal bore thereof. At this time, the rigid rod 26 may completely be removed out of the tube 24, as shown in FIG. 3. However, the tube 24 remains within the self-retaining catheter 40. Further, the outer end of the self-retaining catheter 40 engages in the annular groove 16 on the forward face of the stopper 12 to hold the stopper 12 and thus the tube 24 in place on the self-retaining catheter 40.

Figure 4:
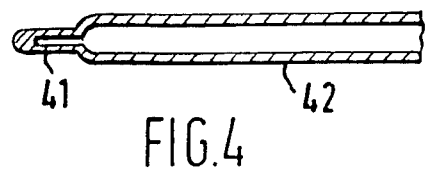
FIG. 4 is a fragmentary view of the longitudinal section of a modification of the present invention.
Figure 5:
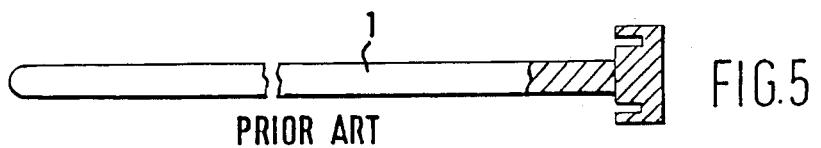
FIG. 5 is a longitudinal section of a prior art obturator.

FIG. 4 shows a modification of the aforementioned embodiment of the present invention wherein the tube 24A has its forwad end 24B made of a hard material. This can prevent the forward end 24B of the tube 24A from being torn by the forward end of the rigid rod.

I claim:

1. An improved combination of a catheter, having a specified internal diameter, and a catheter obturator, having a resilient obturator tube with an external diameter that is at least the catheter internal diameter when said obturator tube is in a relaxed state and is less than the catheter internal diameter when said obturator tube is in an elongated state, a stopper attached to a proximal end of said obturator tube, and manipulating means connectable to said stopper for selectively elongating and relaxing said obturator when said obturator tube is disposed within said catheter with the catheter internal and obturator external diameters aligned.

2. The catheter obturator claimed in claim 1 wherein said manipulating means includes a rigid rod extending through a bore in said stopper and within said obturator tube, said rigid rod having a length greater than the distance between the stopper and a closed end of the obturator tube, and engaging means associated with the stopper for selectively holding said rigid rod against motion with respect to said stopper in an extended position wherein the rod moves the closed end of the obturator tube distally of the stopper to elongate said obturator tube.

3. The catheter obturator claimed in claim 2 wherein said engaging means includes a bushing adjacent the rigid rod and a cap nut threadable onto said stopper for cooperative deformation of the bushing against said rigid rod.

4. An improved method for obturating a catheter having a specified internal diameter, comprising the steps of:
elongating a resilient obturator tube, from a relaxed length where an external diamter of the obturator tube is at least the internal diameter of the catheter, to an extended, longer length where the external diameter of the obturator tube is less than the internal diameter of the catheter,
inserting the elongated obturator tube within said catheter,
reducing the obturator tube while within the catheter from the extended length to a reduced length where the external diameter of the obturator tube is about equal to the internal diameter of the catheter.

5. An improved method for obturating a catheter having a specified internal diameter, comprising the steps of:
inserting a rigid rod within a resilient obturator tube having an external diameter at least the internal diameter of the catheter until a distal end of the rigid rod abuts a closed end of the obturator tube distal of the open end of the obturator tube,
extending the distal end of the rigid rod further from the open end of the obtruator tube, thereby
elongating the obturator tube and reducing the external diameter of the obturator tube to an elongated diameter that is less than the catheter internal diameter, and
holding the rigid rod against movement with respect to the stopper; then
inserting the elongated obturator tube into the catheter; then
releasing the rigid rod for movement with respect to the stopper,
retracting the distal end of the rod toward the stopper until the obturator tube is substantially relaxed, thereby
expanding the external diameter of the obturator tube to about the catheter internal diameter.

* * * * *